United States Patent  
Burd et al.

(10) Patent No.: US 6,627,153 B1  
(45) Date of Patent: Sep. 30, 2003

(54) INTEGRATED ASSAY FOR ORGAN FUNCTION, DRUGS AND/OR ONE OR MORE METABOLITES

(76) Inventors: John F. Burd, 5659 Glenstone Way, San Diego, CA (US) 92121; Steven V. Edelman, UCSD Veterans Administration Medical Center, Department of Metabolism/Endocrinology 3350 La Jolla Village Dr., Suite 111G, San Diego, CA (US) 92161

( * ) Notice: Subject to any disclaimer, the term of this patent is extended or adjusted under 35 U.S.C. 154(b) by 0 days.

(21) Appl. No.: 09/914,655

(22) PCT Filed: Mar. 1, 2000

(86) PCT No.: PCT/US00/05369

§ 371 (c)(1),  
(2), (4) Date: Aug. 31, 2001

(87) PCT Pub. No.: WO00/54051

PCT Pub. Date: Sep. 14, 2000

Related U.S. Application Data

(63) Continuation-in-part of application No. 09/264,249, filed on Mar. 8, 1999, now abandoned.

(51) Int. Cl.$^7$ .................................................. G01N 33/48  
(52) U.S. Cl. .......................... 422/58; 422/61; 436/169; 436/63; 436/95  
(58) Field of Search ...................... 422/58, 61; 436/164, 436/169, 811, 815, 816, 817, 901, 95–99, 63

(56) References Cited

U.S. PATENT DOCUMENTS

| | | | | |
|---|---|---|---|---|
| 4,752,568 A | * | 6/1988 | Danielson et al. | 435/7.93 |
| 5,508,173 A | * | 4/1996 | Amano et al. | 435/28 |
| 5,695,949 A | * | 12/1997 | Galen et al. | 435/14 |
| 6,306,347 B1 | * | 10/2001 | Mason et al. | 422/58 |

FOREIGN PATENT DOCUMENTS

| EP | 0387630 | * | 9/1990 |
|---|---|---|---|
| EP | 0794424 | * | 9/1997 |

* cited by examiner

Primary Examiner—Lyle A. Alexander

(57) ABSTRACT

A test device that assesses the concentration of an organ marker, a drug marker and a metabolite associated with the drug/organ interaction.

2 Claims, No Drawings

INTEGRATED ASSAY FOR ORGAN FUNCTION, DRUGS AND/OR ONE OR MORE METABOLITES

This is a national stage application of PCT/4300/05369, filed Mar. 1, 2000, which is a continuation in part of Ser. No. 09/264,249, filed Mar. 8, 1999, now abandoned.

FIELD OF THE INVENTION

This invention relates to an integrated assay system, more specifically, to assessing the effectiveness of a drug and the organ function of a patient by measuring the concentrations of an organ marker, a drug and/or one or more metabolites with an integrated test system.

BACKGROUND INFORMATION

Many drugs are currently available to treat diseases such as diabetes mellitus, cancer, hypertension, seizure disorders and infection. However, a number of these drugs can be dangerous and have been shown to result in organ damage in certain patients. On occasion, permanent organ damage can go undetected because potential drug side effects are not monitored effectively. Such organ damage may eventually require an organ transplant or even lead to death.

For example, the drug troglitazone helps diabetes patients to control abnormally high blood glucose levels. Most patients tolerate this drug well and develop no lasting harmful side effects. Others tolerate the drug initially, but suddenly develop liver disease. Fortunately, for most of these patients, organ damage can abate or disappear when the drug is discontinued. However, some patients can develop permanent liver damage, which may result in death or require a transplant, especially if the patient's liver function is not being monitored regularly. Accordingly, liver function tests are strongly recommended before and periodically during treatment with troglitazone.

Drug-related organ damage is not limited to the liver, since most major organs can be damaged from a number of abnormal physiological conditions. For example, patients taking the drug metformin, which is used mainly to manage diabetes mellitus, can develop kidney dysfunction. Other drugs implicated in conditions leading to organ damage include phenytoin, used for treating seizure disorders, which can lead to liver and kidney damage; methyldopa, for treating hypertension can lead to liver damage; docetaxel, gemutabine, bicalutamide, nilutamide, all of which are used to treat cancer and can lead to liver damage; antibiotics such as streptomycin, which can lead to liver and kidney damage; isoniazid, for treating tuberculosis, which can lead to liver damage; and tolcopone, for treating Parkinson's disease, which can lead to liver damage. Thus, it is critical to monitor organ function in patients receiving these and other potentially dangerous drugs so that the dosage can be altered or even discontinued at the first indication of organ damage.

Organ function tests alone do not always give a realistic indication of the patient's overall condition. There are instances where it also would be beneficial to monitor a drug and/or metabolite affected by the drug at the same time as organ function, so that a more accurate diagnosis of the condition can be made. For example, possible organ damage indicated by a reduced organ function assay could be due to a pre-existing underlying condition, rather than the drug therapy itself. In these situations, potentially life-threatening conditions could go undiagnosed. In addition, it would be beneficial to measure the drug concentration and/or metabolite concentration at the same time as organ function to find the optimal dosage of the drug to manage the condition. However, there are no integrated test systems that measure the concentration of organ marker, drug and/or one or more metabolites that are simple and convenient to use by a physician in the office or at home by the patient.

Currently, organ function assays require a venipuncture blood sample and are typically performed in a clinical lab using complicated techniques and expensive instrumentation. Results from these clinical lab tests are usually not available to the doctor and patient for several days. This delay in reporting can decrease the value of the test result. The physician can even neglect to relay the test result to the patient until the next visit, which could be several months later.

Therefore, a need exists for conveniently and quickly measuring concentrations of organ marker, drug and/or one or more metabolites in combination to give a better evaluation of the therapeutic effectiveness of the drug and the well-being of a patient. Currently, no such test system exists. Particularly useful would be an integrated instrument for determining a patient's overall organ function that could be used at the doctor's office, or better yet, at home by the patient. The present invention satisfies these needs and provides related advantages as well.

SUMMARY OF THE INVENTION

The present invention provides a method for assessing the effectiveness of a drug therapy and the organ function of a patient by measuring the concentration of an organ marker, drug and/or one or more metabolites in a patient's body fluid. The invention also provides an integrated test system for performing the method of the invention.

DETAILED DESCRIPTION OF THE INVENTION

The methods and test system of the present invention provide an integrated assay that allows a patient taking a drug or the patient's physician to assess the patient's organ function and the efficacy of drug treatment. In addition, the present invention allows the dosage of the drug to be optimized for the condition treated. Such a system is also useful to reduce the risk of organ damage caused by drugs used to treat various conditions, such as diabetes mellitus, cancer, hypertension and conditions treated with antibiotics. Prior to this invention, multiple tests to assess a patient's organ function could be performed using well known methods. However, these tests were performed in a clinical laboratory using a venipuncture blood sample with expensive equipment and complicated procedures. In addition, separate tests were performed for organ function, drug and metabolite concentrations. The present test system allows the doctor to use an integrated test system to measure the concentration of organ marker, drug and/or one or more metabolites at the office. Even better, the present invention allows the patient to perform the testing at home, thereby providing a quick, accurate and complete picture of the patient's organ function and the effectiveness of the drug therapy.

The present invention provides an integrated test system and method for assessing the effectiveness of a drug therapy and organ function of a patient by measuring the concentration of organ marker, drug and/or one or more metabolites. The information provided by the testing for organ marker, drug and/or one or more metabolites is particularly useful because an elevated organ marker concentration by itself does not necessarily provide any information about a possible cause. For example, a pre-existing condition, such as cirrhosis of the liver, rather than a drug, could be responsible for a marked increase in organ marker concentration. Thus, the physician could fail to diagnose a potentially life-threatening situation. By also knowing the concentration of the drug and/or metabolite in the body fluid sample, the physician is able to assess what effect the drug has on the condition and adjust the dosage accordingly.

In one embodiment, the present invention comprises a method for assessing the organ function of a patient using an integrated test device by applying a body fluid sample to a first test strip containing a signal-producing system indicative of organ marker concentration present in the body fluid sample, applying a body fluid sample to a second test strip containing a signal-producing system indicative of drug concentration present in the body fluid sample and applying a body fluid sample to a third test strip containing a signal-producing system indicative of metabolite concentration present in the body fluid sample. Alternatively, the method comprises applying body fluid sample to the first and second test strips, but not to the third. Also alternatively, the method comprises applying body fluid sample to the first and third test strips, but not to the second. Finally, the method comprises applying body fluid sample to the second and third test strips, but not to the first.

The present invention can also be used to assess the effectiveness of a drug therapy to optimize the dosage of the drug. For example, in a diabetic patient, if the concentration of drug is substantially higher than an efficacious level, organ damage could result. The patient should then seek the doctor's advice immediately. In addition, if the drug dosage is too high, the concentration of glucose may become too low, which could lead to the problems associated with hypoglycemia, including coma and even death. Conversely, too small a dosage of drug would be indicated by elevated concentrations of glucose and by sub-therapeutic concentrations of the drug in the bloodstream. If glucose levels remain too high for too long, other long-term complications may result. However, in combination with the organ function assay, the latter situation would inform the patient whether the dosage should be increased or whether therapy should be discontinued due to possible organ damage. In any event, by measuring organ function and/or drug concentration and/or glucose concentrations, the patient or physician can quickly adjust the dosage or discontinue taking the drug to prevent permanent organ damage or even death.

As used herein, the term "organ marker" refers to any analyte present in a body fluid that can indicate organ damage. Thus, the concentration of organ marker provides an indication of organ function. Specifically, the concentration of organ marker indicates whether organ damage has occurred or is occurring in the patient. The user can select which organ to assess by selecting a particular organ marker for testing using the present invention. Examples of organ markers for liver function include: alanine aminotransferase (ALT), also known as serum glutamate pyruvate transaminase (SGPT); aspartate aminotransferase (AST), also known as serum glutamic oxaloacetic transaminase (SGOT) and gamma glutamyl transferase (GGT). Markers for other organs include alkaline phosphatase; creatine kinase; creatinine; amylase and lactic dehydrogenase. One skilled in the art would understand that any other analyte present in a body fluid for assessing organ damage is also encompassed by the present invention.

Depending on the organ marker chosen for measurement, assessment of any particular organ's function can be made. For example, ALT is normally found in the liver. In the event of liver damage, the enzyme leaks into the bloodstream where concentrations become elevated compared to normal. Elevated levels of ALT may therefore indicate hepatocellular injury, which is found in a small percentage of diabetes patients using the insulin-sensitizing drug, troglitazone.

ALT catalyzes the reaction between L-alanine and α-ketoglutarate producing pyruvate and glutamate. In one system to measure ALT concentrations, pyruvate is oxidized by pyruvate oxidase producing hydrogen peroxide. The hydrogen peroxide formed, in the presence of peroxidase, changes the color of an indicator dye. The kinetics of the color development are proportional to the ALT activity in the body fluid sample. Therefore, ALT activity can be readily measured using well known methods.

There are several examples of such methods. The first kinetic determination of ALT activity in serum used a UV photometric measurement of NADH consumption. Wroblewski et al., *Proc. Soc. Exp. Biol. Dem.* 91:569 (1956). This continues to be the most frequently used procedure. However, it was later modified to provide optimal substrate concentration for enzyme measurement. Bergmeyer et al., *Methods of Enzymatic Analysis, 2nd English Ed.* Academic Press, Inc., New York (1974) p. 727. To date, there are many systems and methods to detect and quantify ALT in biological fluids. For example, methods and multilayer dry analytical elements for assaying various enzymes, including ALT, are described in U.S. Pat. No. 5,508,173, issued Apr. 16, 1996, to Amano et al.; U.S. Pat. No. 5,462,858, issued Oct. 31, 1995, to Bale Oenick et al.; U.S. Pat. No. 5,059,526, issued Oct. 22, 1991, to Arai et al.; U.S. Pat. No. 5,066,462, issued Nov. 19, 1991, to Kawasaki et al.; U.S. Pat. No. 4,937,047, issued Jun. 26, 1990, to Kobayashi et al.; U.S. Pat. No. 4,897,347, issued Jan. 30, 1990, to Katsuyama et al.; and U.S. Pat. No. 4,503,145, issued Mar. 5, 1985, to Katsuyama et al., each of which is incorporated by reference herein. One skilled in the art would therefore be able to make and use a test strip for detecting ALT.

When analyzed at 37° C., the normal adult reference range for ALT activity is up to 55 U/L, depending on the method used. Men typically exhibit slightly higher values than women. Normal newborns have been reported to show a reference range of up to double that of the adult upper level. However, these values to adult levels by approximately 3 months of age.

AST is normally found in the liver, heart and skeletal muscle. In the event of liver or heart damage, AST leaks into the bloodstream where concentrations become elevated as compared to normal. Elevated levels of AST may therefore indicate hepatocellular injury.

AST catalyzes the reaction between α-ketoglutatate and alanine sulfate. The resulting pyruvate, catalyzed by pyruvate oxidase, is oxidized in the presence of oxygen. The hydrogen peroxide formed in the presence of peroxidase changes the color of an indicator dye. The kinetics of the color development are proportional to AST activity in the body fluid sample. Therefore, AST activity can be readily measured using well known methods.

Examples of such methods are as follows. The first kinetic determination of AST activity in serum used a UV photometric determination of NADH consumption. Karmen et al., *J. Clin. Invest.* 34:126 (1955). This methodology was refined to an optimal substrate concentration. Bergmeyer et al., *Methods of Enzymatic Analysis, 2nd English Ed.*, Academic Press, Inc., New York (1974) p. 727. Many others have improved this procedure even further by providing test kits where the reaction can be evaluated by reflectance photometry. For example, methods and multilayer dry analytical elements for assaying various enzymes, including AST, are described in U.S. Pat. No. 5,462,858, issued Oct. 31, 1995, to Bale Oenick et al; U.S. Pat. No. 5,059,526, issued Oct. 22, 1991, to Arai et al.; U.S. Pat. No. 4,937,047, issued Jun. 26, 1990 to Kobayashi et al.; U.S. Pat. No. 4,923,800, issued May 8, 1990, to Ly; U.S. Pat. No. 4,897,347, issued Jan. 30, 1990, to Katsuyama et al.; U.S. Pat. No. 4,728,604, issued Mar. 1, 1998, to Moller; U.S. Pat. No. 4,591,553, issued May 27, 1986, to Deneke et al.; U.S. Pat. No. 4,503,145, issued Mar. 5, 1985, to Katsuyama et al.; U.S. Pat. No. 4,450,232, issued May 22, 1984, to Sanford et al.; U.S. Pat. No. 3,891,507, issued Jun. 24, 1975, to Breuer; and U.S. Pat. No. 3,875,014, issued Apr. 1, 1975, to Forgione, all of which are incorporated by reference herein. One skilled in the art would therefore be able to make and use a test strip for detecting AST.

When analyzed at 37° C., the normal adult reference range for AST activity is between 5 and 34 U/L, depending on the method used. Men typically exhibit slightly higher values than women. Normal newborns have been reported to show a reference range of up to double that of the adult upper level. However, these values decline to adult levels by approximately 6 months of age. In addition, for patients with unexplained AST elevations, liver and muscle disease can be biochemically excluded by the finding of normal serum levels of ALT and creatine kinase.

The quantitative determination of GGT is also used to indicate potential organ damage in a patient. GGT catalyzes the transfer of the gamma glutamyl group from one peptide to another or to an amino acid. Recent studies suggest that GGT may be involved in the transport of amino acids through cell membranes. The concentration of GGT is primarily elevated in liver disease and hepatobiliary obstruction.

The original procedure for measuring GGT concentrations involved adding glycylglycine to a γ-glutamyl-4-nitroanilide reagent to serve as the glutamyl receptor. Adolph et al., *Enzyme Diagnosis in Diseases of the Heart, Liver and Pancreas*, Basel, N.Y., (1981) p. 109. However, there has been much activity in developing tests, including test kits for measuring GGT levels. For example, methods and multilayer dry analytical elements for assaying various enzymes, including GGT, are described in U.S. Pat. No. 4,916,059, issued Apr. 10, 1990, to Shigeki Kageyama et al, which is incorporated by reference herein. In addition, there has been much work directed to assaying GGT activity with different reagents and different solutions. For example, such methods and reagents are described in U.S. Pat. No. 5,474,906, issued Dec. 12, 1995, to Satoh; U.S. Pat. No. 5,126,245, issued Jun. 30, 1992, to Motoyama et al.; U.S. Pat. No. 5,116,730, issued May 26, 1992, to Artiss et al.; U.S. Pat. No. 5,096,812, issued Mar. 17, 1992, to Rachel et al.; U.S. Pat. No. 5,081,259, issued Jan. 14, 1992, to Artiss et al.; and U.S. Pat. No. 4,943,526, issued Jul. 24, 1990, to Rauscher et al., all of which are incorporated by reference herein. One skilled in the art would therefore be able to make and use a test strip for detecting GGT.

Normal GGT values at 37° C. for men are between 11 and 50 U/L. Values for women are slightly lower. GGT values will vary with the method used, whether calorimetric or kinetic.

Troglitazone is an antidiabetic drug that lowers blood glucose by improving target cell response to insulin without increasing pancreatic insulin secretion. It also decreases insulin resistance. It decreases hepatic glucose output and increases insulin-dependent glucose disposal in skeletal muscle and possibly liver and adipose tissue. *Drug Facts and Comparisons*, 1998 Ed., Facts and Comparisons, St. Louis, Mo. p.628. A serious complication that can occur with troglitazone is liver damage, ranging from reversible jaundice to permanent liver damage necessitating liver transplant. In a small percentage of patients, death may occur. Therefore, organ function tests should be carried out before and periodically during troglitazone therapy.

Table 1 lists examples of organ markers to detect liver damage and associated metabolites, which can be useful for monitoring when using troglitazone therapy, all of which are encompassed within the test system and methods of the present invention.

TABLE 1

| LIVER | | |
|---|---|---|
| Organ Marker | Drug | Metabolite |
| ALT | troglitazone | glucose |
| AST | pioglitazone | fructosamine |
| GGT | | $HbA_{1C}$ |
| other markers | other glitazone drugs | other glycated proteins |

A variety of other drugs can cause liver damage. These drugs include tolcapone, acetaminophen and a variety of antibiotics. Therefore, regular monitoring of liver markers during drug therapy with these drugs would be very useful.

Metformin is another drug for treating diabetes mellitus. It lowers both basal and postprandial plasma glucose levels by reducing intestinal absorption and hepatic glucose production and by improving insulin sensitivity. With metformin therapy, insulin secretion remains unchanged while fasting insulin levels and day-long plasma insulin response may actually decrease. *Drug Facts and Comparisons*, 1998 Ed., Facts and Comparisons, St. Louis, Mo., pp. 620–627. Metformin is contraindicated in patients with renal dysfunction or conditions that compromise renal function, such as cardiovascular collapse, acute myocardial infarction and septicemia. Metformin is excreted unchanged in the urine and does not undergo hepatic metabolism nor biliary excretion. Following oral administration, 90% of the absorbed drug is eliminated via the renal route within the first 24 hours.

A serious complication with metformin is the possibility of lactic acidosis. Although very few patients taking metformin have developed lactic acidosis (one in 33,000 patients taking the drug over a year), about 50% of the cases of lactic acidosis result in death. Lactic acidosis is indicated by elevated blood lactate levels greater than 5 mmol/L, decreased blood pH, electrolyte disturbances and an increased lactate:pyruvate ratio.

Table 2 lists organ markers that can be detected in kidney damage and associated metabolites that can be useful to monitor during metformin or related drug therapies, all of which are encompassed within the integrated test system and methods of the present invention.

TABLE 2

KIDNEY

| Organ Marker | Drug | Metabolite |
| --- | --- | --- |
| serum creatinine | metformin | lactic Acid |
| urine creatinine | phenformin | glucose |
| other markers |  | fructosamine |
|  |  | HbA$_{1C}$ |
|  |  | creatinine |
|  |  | other glycated proteins |

Other drugs, such as ibuprofen and acetaminophen can cause kidney damage.

In addition, renal failure can be caused by other drugs such as streptomycin and other antibiotics, cimetidine, clofibrate, phenytoin and other anticonvulsants and hydroclorothiazide. Therefore, regular renal monitoring of patients taking metformin, ACE inhibitors or other drugs, is essential, especially for those already at risk for renal dysfunction.

Renal function is typically monitored by measuring the glomerular filtration rate (GFR). This value is determined by measuring serum creatinine levels. Renal disease or renal dysfunction is suggested by serum creatinine levels $\geq 1.5$ mg/dL for males and $\geq 1.4$ mg/dL for females. In addition, creatinine is useful as a standard to measure the concentration of other analytes. Spierto et al. *Clinica Chimica Acta* 264:227–232 (1997), which is incorporated herein by reference. Because urine flow volume changes unpredictably during the day, the concentration of other analytes will vary. But since the amount of creatine phosphate, which spontaneously forms creatinine, is roughly proportional to the muscle mass of the body, and since the glomerular filtration rate is fairly constant in a healthy patient, the spontaneous formation of creatinine is characteristic of each patient and normally proceeds at a constant rate from day to day. Vestergaard et al., *J. Lab. Clin. Med.* 51:211–218 (1958). If the glomerular filtration rate is reduced by the effects of metformin, for example, this will appear as a significant change in creatinine levels. In blood, renal dysfunction is indicated by increased creatinine levels, while in urine it is indicated by decreased creatinine levels.

The present invention contemplates a test system comprising a test device containing a system capable of signaling the concentration of organ marker present in an unprocessed body fluid sample.

Determining the concentration of organ marker alone does not necessarily provide the cause of organ damage. Although it is useful to detect possible organ damage in a patient, it is also useful to correlate that organ damage with a potential cause, for example a drug. Furthermore, it is extremely important to alter the dosage or discontinue taking the drug in a timely manner at the first indication of organ damage.

Other drugs used treating a variety of conditions can also be toxic to the patient. For example, cancer drugs such as docetaxel, gemcitabine, bicalutadmide and nilutamide can all cause liver damage. Another drug that can cause liver toxicity is tolcapone. Other drugs that can cause organ damage are not limited to these examples but may extend to antibiotics, cortisone-based drugs, drugs used to treat hypertension and dyslipidemia, drugs to treat seizure disorders and the like. Therefore, the present invention contemplates determining the concentration of any drug that can cause, or is suspected of causing, organ damage in a patient.

In one embodiment, the present invention comprises test strips made up of a bibulous material impregnated with the dried residue of a reagent system that changes color in response to the concentration of drug. The test strip contains all the reagents necessary for the test, needing only the addition of the body fluid sample to activate the reagents. Test strips for detecting drugs in a body fluid sample can be prepared by methods known to those skilled in the art. For example, U.S. Pat. No. 4,752,448, issued Jun. 21, 1988, to Wells et al., which is incorporated herein by reference, describes a diagnostic test paper containing the reagents necessary to detect abuse-type drugs. In addition, U.S. Pat. No. 5,457,054, issued Oct. 10, 1995, to Geisinger et al., which also is incorporated herein by reference, describes a test kit and method for the qualitative determination of an illicit drug. For example, to test for drugs such as cocaine, morphine, heroine, PCP, amphetamines, methadone, codeine and other opiates, benzodiazepines and related molecules and phenothiazines, the reagent material is a mixture of potassium iodide and hexachloroplatinate. However, it would be routine for one skilled in the art to make and use test strips containing the reagents to detect any drug desired.

Another aspect of the present invention is measuring the concentration of a metabolite in the body fluid sample. As used herein, the term "metabolite" refers to any component of the body fluid sample that can be used to monitor a specific disease. For example in diabetes mellitus, glucose, fructosamine and glycated hemoglobin, namely hemoglobin A$_{1c}$ (HbA$_{1c}$) are metabolites that can be measured by the present invention. In renal dysfunction, metabolites that can be measured by the present invention include lactic acid and creatine.

In one embodiment, the test device comprises a multilayer test device for analyzing fructosamine concentration. The multilayer test device contains a signal-producing system that is an indicator capable of being reduced by fructosamine such as certain dyes, including chromogenic dyes or fluorescent reagents. The multilayer test device is described more in U.S. Pat. No. 5,470,752 to Burd et al. and U.S. Pat. No. 5,695,949 to Galen et al., both of which are incorporated herein by reference. However, the present invention relates to other metabolites and is not limited to fructosamine. Furthermore, one skilled in the art would be able to use similar methods and devices to detect other metabolites contemplated within the present invention.

The "body fluid sample" from the patient that is analyzed for organ marker, drug and/or one or more metabolites associated with a particular condition, can be any unprocessed biological fluid that contains or is suspected of containing these analytes including whole blood, urine, saliva, interstitial fluid and tears. The body fluid is "unprocessed," meaning that the body fluid need not be processed, such as by separation techniques and the like, prior to testing. The body fluid can be applied directly to the test device, without separating plasma or serum from whole blood. If required, within the test device itself the body fluid can be separated or otherwise processed, such as by a red blood cell separation layer (see, e.g., U.S. Pat. No. 5,725,774 to Neyer).

The body fluid sample used for measuring the concentration of organ marker can be the same type of body fluid sample used to measure the concentration of drug or metabolite. For instance, whole blood can be used for the organ marker portion, the drug and the metabolite aspect of the invention. Alternatively, the body fluid sample or samples can be different types of body fluids, such as using urine to determine the concentration of organ marker and a sample of whole blood to assay for drug and a sample of saliva to assay for the metabolite. Because the present invention can be used advantageously in the home environment by the patient, the preferable body fluid for the organ marker, drug and/or one or more metabolites analysis is whole blood and more preferably whole blood taken from a finger or earlobe puncture. Using finger sticks, pipettes, droppers or the like can be used to collect the blood sample for the test.

The body fluid sample or samples from which organ marker, drug and/or one or more metabolites are measured can be the same sample or separate samples, depending upon how the sample is taken from the patient. By "separate" samples is meant individual body fluid samples, such as two or more samples, that can be the same type of body fluid, as described above. For example, where the body fluid samples are each a drop of blood, such as from separate pricks of a patient's finger, they are "separate" or "different" samples. Alternatively, the body fluid can be collected from the patient, such as drawing a sample of blood, in which case the body fluid sample for analyzing organ marker, drug and/or one or more metabolites would be taken from the collected specimen and are considered the same sample. Additional body fluid samples can be used, such as a fourth body fluid sample or more when analyzing more than one metabolite or for measuring optional analytes.

The present invention provides methods for assessing the organ function of a patient using an integrated test device by measuring the concentration of organ marker, drug and/or one or more metabolites in a body fluid sample. A body fluid sample is applied to a first test strip containing a signal-producing system indicative of organ marker concentration present in the body fluid sample. A body fluid sample is also applied to a second test strip containing a signal-producing system indicative of drug concentration present in the body fluid sample. A body fluid sample is also applied to a third test strip containing a signal-producing system indicative of metabolite concentration present in the body fluid sample. Alternatively, the body fluid sample can be applied to any combination of two of the three test strips described herein.

The present invention also provides an integrated test system for assessing the organ function of a patient. The integrated test system comprises a means for measuring the concentration of an organ marker, a means for measuring the concentration of a drug and a means for measuring the concentration of a metabolite. Alternatively, the integrated test system can comprise any combination of two of the three means described herein.

A suitable apparatus used in the integrated test system can read the results of the organ marker, drug and/or one or more metabolites test. If further optional analytes are also measured, corresponding test devices can be used with the present invention. Therefore, such an apparatus will be constructed to specifications that are dependent on the signal-producing system of the test and the automatic determining means that is responsive to the signal produced. For example, if the automatic concentration determining means, or read-out, is color production, the apparatus can contain a determining means that is a spectrophotometer or reflectance meter. Other spectrophotometers that can be used with the present invention can measure, for example, fluorescence, absorbance, or transmittance. If the read-out is electrochemical, a miniaturized electrode system can be employed. For example, it is well known in the art how to measure glucose electrochemically, as taught, for instance, by Higgins et al. in U.S. Pat. No. 4,545,382, Parks et al. in U.S. Pat. No. 4,999,582 and White in U.S. Pat. No. 5,243, 516, each of which is incorporate by reference herein. More than one automatic determining means can be present in the apparatus. For example, an electrode can be present for measuring the concentration of glucose and a reflectance spectrometer can also be present in the apparatus for measuring the concentration of fructosamine. However, other apparatus can be constructed for measuring other organ markers, drugs and metabolites.

In one embodiment the means for measuring the concentration of organ marker comprises a test device containing a system capable of signaling the concentration of organ marker present in an unprocessed body fluid sample from a patient and an apparatus having a receiving port capable of receiving the test device and further having an automatic organ marker concentration determining means responsive to the signal produced coupled to the receiving port. The apparatus further has a display means coupled to the automatic determining means.

In addition, the means for measuring the concentration of metabolite comprises a test device containing a system capable of signaling the concentration of metabolite present in an unprocessed body fluid sample from a patient and an apparatus having a receiving port capable of receiving the test device and further having an automatic metabolite concentration determining means responsive to the signal produced coupled to the receiving port. The apparatus further has a display means coupled to the automatic determining means.

The signal-producing system and reagents used to produce the signal in response to metabolite will depend on which metabolite is to be measured. In one embodiment, the concentration of fructosamine can be measured by the present invention, as described herein.

Test devices containing signal-producing systems capable of signaling the concentration of metabolites such as glucose or fructosamine are well known in the art. For example, U.S. Pat. No. 5,695,949 to Galen et al., which is incorporated herein by reference, describes one such device relating to glucose and fructosamine. Generally, in this art the signal-producing system includes reagents that produce a glucose oxidase enzyme reaction. Glucose and glucose oxidase enzyme react to produce hydrogen peroxide. A peroxidase, such as horse radish peroxidase and a redox indicator, such as o-tolidine, o-dianisidine, 3,3,5,5,-tetramethylbenzidine (TMB), 4-aminoantipyrine and others well known in the art, are capable of being oxidized in the presence of hydrogen peroxide to produce a colored product. A test strip containing these or other reagents of the signal-producing system used in analyzing glucose concentration can be prepared by methods well known in the art, such as described in U.S. Pat. No. 5,304,468 to Phillips et al. and European Patent No. 0 388 782, to Chen, both of which are incorporated herein by reference.

In addition, the means for measuring the concentration of drug comprises a test device containing a system capable of signaling the concentration of drug present in an unprocessed body fluid sample from a subject and an apparatus having a receiving port capable of receiving the test device and further having an automatic drug concentration-determining means responsive to the signal produced coupled to the receiving port. The apparatus further has a display means coupled to the automatic determining means.

The signal-producing system and reagents used to produce the signal in response to a drug will depend on the drug to be measured. In one embodiment, the concentration of troglitazone can be measured.

Test devices containing signal-producing systems for determining the concentration of drugs such as troglitazone are well known in the art. The devices typically contain a reagent selected to be specific for the drug. As an example, U.S. Pat. No. 4,752,448 describes a test device for signaling the presence of common illegal drugs. Other U.S. Patents describing the detection of drugs include U.S. Pat. No. 4,743,541, U.S. Pat. No. 4,650,771, U.S. Pat. No. 4,608,336, U.S. Pat. No. 4,533,493, U.S. Pat. No. 4,404,366, U.S. Pat. No. 4,331,590, U.S. Pat. No. 4,318,981, U.S. Pat. No. 4,292,425, U.S. Pat. No. 4,279,992, U.S. Pat. No. 4,261,974, U.S. Pat. No. 4,226,978 and U.S. Pat. No. 4,039,385. Therefore, one skilled in the art would know how to make and use a test device capable of signaling the concentration of a drug.

Each of the previously described signals can be detected in the device by a single or multiple spectrophotometers. Each of the spectrophotometers can be detect one or more wavelengths of light. In addition, the light used to generate the signals can be from one or multiple light sources, for example light-emitting diodes (LEDs) that can emit one or more wavelengths of light, either singly or in combination.

Although the invention has been described with reference to disclosed embodiments, those skilled in the art will readily appreciate that they are only illustrative of the invention. It should be understood that various modifications can be made without departing from the spirit of the invention. Accordingly, the invention is limited only by the following claims.

We claim:

1. An integrated drug test and organ function test system comprising:

(a) a first strip capable of reacting with an organ marker in a liquid sample, wherein the organ marker is indicative of damage to a predetermined organ;

(b) a second strip capable of reacting with a drug in a liquid sample, wherein the drug can potentially damage the predetermined organ; and (c) a third strip capable of reacting with a metabolite in a liquid sample, wherein the metabolite is associated with at least one of the organ marker and the drug, and a single device capable of accepting the strips when inserted one at time, and discriminating between the strips when inserted, so that (1) when the first strip is inserted, the device measures the organ marker reaction on the first strip and displays the organ marker concentration of the liquid sample, (2) when the second strip is inserted, the device measures the drug reaction on the second strip and displays the drug concentration of the liquid sample, and (3) when the third strip is inserted, the device measures the metabolite reaction on the third strip and displays the metabolite concentration of the liquid sample.

2. The test system of claim 1, wherein the device includes a single measuring device for measuring each reaction.

* * * * *